US012690772B2

(12) United States Patent
Lim et al.

(10) Patent No.: US 12,690,772 B2
(45) Date of Patent: Jul. 28, 2026

(54) APPARATUS AND METHOD FOR ESTIMATING BLOOD PRESSURE

(71) Applicant: SAMSUNG ELECTRONICS CO., LTD., Suwon-si (KR)

(72) Inventors: Hye Rim Lim, Suwon-si (KR); Ui Kun Kwon, Suwon-si (KR); Young Soo Kim, Suwon-si (KR); Chang Soon Park, Suwon-si (KR); Dae Geun Jang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 533 days.

(21) Appl. No.: 18/141,765

(22) Filed: May 1, 2023

(65) Prior Publication Data

US 2024/0225457 A1 Jul. 11, 2024

(30) Foreign Application Priority Data

Jan. 9, 2023 (KR) ........................ 10-2023-0003083

(51) Int. Cl.
| *A61B 5/021* | (2006.01) |
| *A61B 5/00* | (2006.01) |
| *A61B 5/024* | (2006.01) |

(52) U.S. Cl.
CPC .......... *A61B 5/021* (2013.01); *A61B 5/02416* (2013.01); *A61B 5/4561* (2013.01); *A61B 5/7278* (2013.01)

(58) Field of Classification Search
CPC ... A61B 5/4561; A61B 5/1116; A61B 5/7278; A61B 5/02108; A61B 2560/0247; A61B 5/021; A61B 5/02416; A61B 5/022; A61B 8/04; A61B 5/02
See application file for complete search history.

(56) References Cited

U.S. PATENT DOCUMENTS

| 8,585,605 | B2 * | 11/2013 | Sola I Caros | .......... A61B 5/029 |
| | | | | 600/506 |
| 8,738,118 | B2 * | 5/2014 | Moon | ...................... A61B 5/33 |
| | | | | 600/513 |
| 10,602,935 | B2 | 3/2020 | Fuke et al. | |
| 10,660,534 | B2 * | 5/2020 | Lee | ................... A61B 5/02438 |
| 11,241,170 | B2 * | 2/2022 | Kim | ................... A61B 5/02108 |

(Continued)

FOREIGN PATENT DOCUMENTS

| CN | 112135560 | A | * | 12/2020 | ............. A61B 5/021 |
| EP | 3 430 991 | A1 | | 1/2019 | |

(Continued)

*Primary Examiner* — Oommen Jacob
(74) *Attorney, Agent, or Firm* — Sughrue Mion, PLLC

(57) ABSTRACT

Apparatus and method for estimating blood pressure, including a plurality of sensors; and at least one processor configured to: determine situation information and posture information prior to estimation of blood pressure of a user based on data acquired using the plurality of sensors, select a cardiovascular feature from among a plurality of predetermined cardiovascular features based on the situation information and the posture information, generate a blood pressure estimation model based on the cardiovascular feature, the situation information, and the posture information, and estimate the blood pressure of the user based on the generated blood pressure estimation model.

10 Claims, 11 Drawing Sheets

(56)  References Cited

U.S. PATENT DOCUMENTS

| | | | |
|---|---|---|---|
| 11,583,191 B2 | 2/2023 | Schmitt et al. | |
| 11,911,185 B2 * | 2/2024 | Park | A61B 5/7225 |
| 12,290,344 B2 * | 5/2025 | Park | A61B 5/681 |
| 12,377,318 B2 * | 8/2025 | Lee | A61B 5/02108 |
| 2008/0228089 A1 * | 9/2008 | Cho | A61B 5/021 |
| | | | 600/485 |
| 2010/0241011 A1 * | 9/2010 | McCombie | A61B 5/02125 |
| | | | 600/485 |
| 2010/0245237 A1 * | 9/2010 | Nakamura | G06F 3/014 |
| | | | 340/407.1 |
| 2010/0298660 A1 * | 11/2010 | McCombie | A61B 5/0205 |
| | | | 600/595 |
| 2011/0257489 A1 * | 10/2011 | Banet | A61B 5/6801 |
| | | | 600/534 |
| 2014/0236027 A1 * | 8/2014 | Banet | A61B 5/0205 |
| | | | 600/484 |
| 2018/0020990 A1 | 1/2018 | Park et al. | |
| 2018/0263570 A1 * | 9/2018 | Chen | A61B 5/1116 |
| 2019/0159682 A1 * | 5/2019 | Nakajima | A61B 5/02116 |
| 2019/0313915 A1 * | 10/2019 | Tzvieli | G01J 5/12 |
| 2019/0343407 A1 * | 11/2019 | Huijbregts | A61B 5/70 |
| 2019/0350464 A1 * | 11/2019 | Jeon | A61B 5/6898 |
| 2020/0054290 A1 * | 2/2020 | Jang | A61B 5/1102 |
| 2020/0113526 A1 * | 4/2020 | Park | A61B 5/02116 |
| 2021/0030278 A1 | 2/2021 | Choi et al. | |
| 2021/0100456 A1 | 4/2021 | Park et al. | |
| 2021/0282657 A1 * | 9/2021 | Chen | A61B 5/7264 |
| 2024/0016397 A1 * | 1/2024 | Jung | A61B 5/02125 |
| 2024/0172945 A1 * | 5/2024 | Park | A61B 5/7278 |
| 2024/0188834 A1 * | 6/2024 | Kwon | A61B 5/029 |
| 2024/0225457 A1 * | 7/2024 | Lim | A61B 5/1116 |
| 2024/0380904 A1 * | 11/2024 | Esenlik | H04N 19/189 |

FOREIGN PATENT DOCUMENTS

| | | | | |
|---|---|---|---|---|
| JP | 2016-131825 A | 7/2016 | | |
| JP | 6656005 B2 | 3/2020 | | |
| KR | 10-2019-0131306 A | 11/2019 | | |
| KR | 20190131306 A * | 11/2019 | | A61B 5/6898 |
| KR | 10-2021-0014305 A | 2/2021 | | |
| KR | 20240088354 A * | 6/2024 | | A61B 5/1116 |
| WO | 2020/203020 A1 | 10/2020 | | |

* cited by examiner

APPARATUS AND METHOD FOR ESTIMATING BLOOD PRESSURE

CROSS-REFERENCE TO RELATED APPLICATION(S)

This application claims priority under 35 U.S.C. § 119 to Korean Patent Application No. 10-2023-0003083, filed on Jan. 9, 2023, in the Korean Intellectual Property Office, the disclosure of which is incorporated by reference herein in its entirety.

BACKGROUND

1. Field

The disclosure relates to an apparatus and method for non-invasively estimating blood pressure using a plurality of sensors.

2. Description of Related Art

Research on information technology (IT)-medical convergence technology, in which IT and medical technology are combined, is being carried out to address the aging population structure, rapid increase in medical expenses, and shortage of specialized medical service personnel. For example, monitoring of the health condition of the human body may not be limited to a fixed place, such as a hospital, but may instead be expanding to a mobile healthcare sector for monitoring a user's health condition at any time and any place in daily life at home and office.

Electrocardiography (ECG), photoplethysmogram (PPG), and electromyography (EMG) signals are typical examples of bio-signals that indicate an individual's health condition, and various signal sensors are being developed to measure such signals in daily life. For example, a PPG sensor may estimate blood pressure of a human body by analyzing a form of a pulse wave that indicates cardiovascular status and the like.

Research is being conducted on methods for non-invasively estimating blood pressure using a PPG signal without a pressure cuff. However, blood pressure may vary with an environment of the user during the blood pressure measure, and may be affected by, for example, factors such as the posture and mental activity of the user, such that it may be difficult to accurately estimate blood pressure using only the PPG signal measured at a local body part.

SUMMARY

In accordance with an aspect of the disclosure, an apparatus for estimating blood pressure includes a plurality of sensors; and at least one processor configured to: determine situation information and posture information prior to estimation of blood pressure of a user based on data acquired using the plurality of sensors, select a cardiovascular feature from among a plurality of predetermined cardiovascular features based on the situation information and the posture information, generate a blood pressure estimation model based on the cardiovascular feature, the situation information, and the posture information, and estimate the blood pressure of the user based on the generated blood pressure estimation model.

In accordance with an aspect of the disclosure, a method of estimating blood pressure includes acquiring data using at least one sensor from among a plurality of sensors; determining situation information and posture information prior to estimation of blood pressure of a user based on the acquired data; selecting a cardiovascular feature from among a plurality of predetermined cardiovascular features based on the situation information and the posture information; generating a blood pressure estimation model based on the cardiovascular feature, the situation information, and the posture information; and estimating the blood pressure of the user based on the generated blood pressure estimation model.

In accordance with an aspect of the disclosure, a wearable device includes a main body; a strap connected to two ends of the main body; a plurality of sensors configured to acquire data corresponding to a user based on an object contacting the main body; and a processor configured to: while the object contacts the main body, determine situation information and posture information prior to estimation of blood pressure of the user based on the acquired data, select a cardiovascular feature from among a plurality of predetermined cardiovascular features based on the situation information and the posture information, generate a blood pressure estimation model based on the cardiovascular feature, the situation information, and the posture information, and estimate the blood pressure of the user based on the generated blood pressure estimation model.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
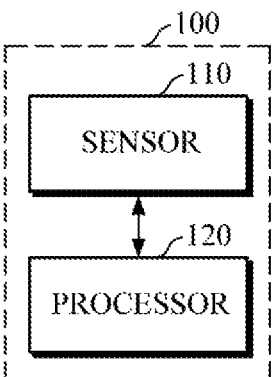
FIG. 1 is a block diagram illustrating an apparatus for estimating blood pressure, according to an embodiment.

Details of embodiments are included in the following detailed description and drawings. Advantages and features of the present disclosure, and a method of achieving the same, will be more apparent from the following embodiments described in detail with reference to the accompanying drawings. Throughout the drawings and the detailed description, unless otherwise described, the same drawing reference numerals may be understood to refer to the same elements, features, and structures. The drawings may not be to scale, and therefore the relative size and depiction of these elements may be exaggerated for clarity, illustration, and convenience.

In embodiments, although the terms first, second, etc. may be used herein to describe various elements, these elements should not be limited by these terms. These terms may be used only to distinguish one element from another. Any references to singular may include plural unless expressly stated otherwise. In addition, unless explicitly described to the contrary, an expression such as "comprising" or "including" may be understood to imply the inclusion of stated elements but not the exclusion of any other elements. Also, the terms, such as "unit" or "module", etc., may be understood as a unit for performing at least one function or operation and that may be embodied as hardware, software, or a combination thereof.

Figure 2:
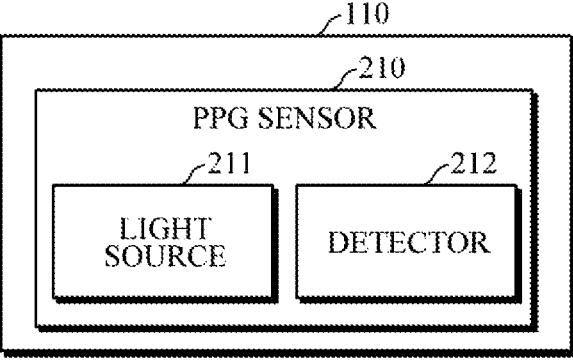
FIG. 2 is a block diagram illustrating an example of a sensor of an apparatus for estimating blood pressure, according to an embodiment.

FIG. 1 is a block diagram illustrating an apparatus for estimating blood pressure according to an embodiment of the present disclosure. FIG. 2 is a block diagram illustrating an example of a sensor of an apparatus for estimating blood pressure.

Various embodiments of an apparatus for estimating blood pressure, examples of which are described below, may be implemented as or by an electronic device including a smartphone, a tablet personal computer (PC), a desktop computer, a laptop computer, or various types of wearable devices, such as wristwatches, bracelets, wristbands, rings, glasses, headbands, and the like. In addition, various embodiments which are described below may be used for estimating a variety of cardiovascular information including not only blood pressure but also arrhythmia, vascular age, skin elasticity, skin age, arterial stiffness, aortic pressure waveform, stress index, fatigue level, and the like.

Referring to FIG. 1, an apparatus 100 for estimating blood pressure includes a sensor 110 and a processor 120.

The sensor 110 may be or include one or a plurality of sensors capable of acquiring a variety of information from a user, and examples of the sensors may include an acceleration sensor, an angular velocity sensor, a geomagnetic sensor, a gyro sensor, a temperature sensor, a pressure sensor, and a photoplethysmogram (PPG) sensor. The sensor 110 may transmit the acquired data to the processor 120. The type of the sensor is not limited thereto.

Referring to FIG. 2, the sensor 110 may include, for example, a PPG sensor 210 for measuring a photoplethysmogram (PPG) signal. The PPG sensor 210 may include a light source 211 for emitting light to an object, and a detector 212 for detecting light, for example light emanated by scattering or reflection from body tissue of the object when light is emitted by the light source 211, in order to measure the PPG signal. In this case, the light source 211 may include at least one of a light emitting diode (LED), a laser diode (LD), and a phosphor, but is not limited thereto. The detector 212 may include a photo diode, a photo transistor (PTr), an image sensor (e.g., complementary metal-oxide semiconductor (CMOS) image sensor), etc., but is not limited thereto.

In embodiments, the object may be a body part that may be in direct or indirect contact with, or adjacent to, the PPG sensor, and may be a body part at which a pulse wave may be easily measured based on a PPG signal. For example, the object may be an area on the wrist that is adjacent to the radial artery and may include an upper part of the wrist where venous blood or capillary blood passes. When a pulse wave is measured on a skin surface of the wrist under which the radial artery passes, the measurement may be relatively less affected by external factors, such as the thickness of the skin tissue inside the wrist, which cause a measurement error. However, the object is not limited to the above examples, and may be a peripheral body part, such as a finger, a toe, or the like, which is a region having a high blood vessel density in the human body.

Upon receiving a request for estimating blood pressure from a user, the processor 120 may generate a control signal for controlling the sensor 110 and may transmit the control signal to the sensor 110. In addition, the processor 120 may receive data from the sensor 110 and may estimate blood pressure by analyzing the received data.

The processor 120 may estimate blood pressure based on information obtained or received prior to estimation of a user's blood pressure based on the data acquired by the plurality of sensors.

For example, the processor 120 may recognize a user's situation information and posture information prior to estimation of the user's blood pressure based on the data acquired by the plurality of sensors. In this case, the situation information may include at least one of the user's mental activity, physical activity, and surrounding environment, and the posture information may indicate at least one of a sitting posture, a supine posture, and a standing posture.

For example, the processor 120 may detect an increase and decrease in the user's heart rate based on the PPG signal acquired by the PPG sensor, and upon detecting an increase in the user's heart rate, the processor 120 may recognize that the user has performed or is performing a mental activity (e.g., mental arithmetic). In addition, the processor 120 may also recognize that the user's environment (e.g., cold pressor) is changed based on a temperature change detected by a temperature sensor or a pressure change detected by a pressure sensor. In addition, the processor 120 may recognize that the user has performed or is performing a physical activity (e.g., exercise) based on a change in data acquired by an acceleration sensor, an angular velocity sensor, or a geomagnetic sensor, etc., and may also recognize whether the user's posture corresponds to one of a sitting posture, a supine posture, and a standing posture.

Next, the processor 120 may determine or select one of a plurality of predefined or predetermined cardiovascular features based on the recognized situation information and posture information. In this case, the cardiovascular features may include a cardiac output (CO) feature and a total peripheral resistance (TPR) feature.

In embodiments, a variation in mean arterial pressure (MAP) may be proportional to cardiac output (CO) and total peripheral resistance (TPR), as shown for example in Equation 1 below.

$$MAP - RAP = CO \times TPR \qquad \text{(Equation 1)}$$

Herein, MAP may denote a mean arterial pressure when blood is ejected from the left ventricle of the heart, and RAP may denote a mean arterial pressure when blood enters the right atrium of the heart. Accordingly, MAP-RAP may denote a difference in MAP between the left ventricle and the right atrium, in which MAP in the right atrium is usually within a range of 3 mmHg to 5 mmHg, such that a value obtained by multiplying CO values and TPR values is similar to MAP in the left ventricle or MAP of the upper arm. Thus, if absolute actual CO values and TPR values are known, MAP may be obtained from the aorta or the upper arm. However, it may be difficult to estimate absolute CO values and TPR values based on a PPG signal measured at a local body part, and blood pressure may be estimated by extracting a cardiac output (CO) feature and a total peripheral resistance (TPR) feature (hereinafter referred to as a "TPR feature") from a bio-signal (e.g., PPG signal) and using the extracted CO feature and TPR feature.

The processor 120 may determine at least one or more of a plurality of predefined CO features and TPR features based on the recognized situation information and posture information.

The following Table 1 and Table 2 show predefined TPR features and CO features according to the recognized situation information and posture information.

TABLE 1

| Feature | Sitting posture | Supine posture | Standing posture |
|---|---|---|---|
| Mental activity | $f_{TPR}1$ | $f_{TPR}3$ | $f_{TPR}1$ |
| Surrounding environment | $f_{TPR}2$ | $f_{TPR}2$ | $f_{TPR}1$ |
| Physical activity | $f_{TPR}5$ | $f_{TPR}4$ | $f_{TPR}5$ |

TABLE 2

| Feature | Sitting posture | Supine posture | Standing posture |
|---|---|---|---|
| Mental activity | $f_{co}2$ | $f_{co}3$ | $f_{co}2$ |
| Surrounding environment | $f_{co}3$ | $f_{co}2$ | $f_{co}1$ |
| Physical activity | $f_{co}1$ | $f_{co}4$ | $f_{co}4$ |

For example, upon recognizing, using the PPG sensor and the gyro sensor, that a user is performing or has performed a mental activity and is in a sitting posture, the processor 120 may determine $f_{TPR}1$ as the TPR feature among the TPR features, and $f_{co}2$ as the CO feature among the CO features. Further, upon recognizing, using the acceleration sensor, that a user is performing or has performed a physical activity and is in a standing posture, the processor 120 may determine $f_{TPR}5$ as the TPR feature among the TPR features, and $f_{co}4$ as the CO feature among the CO features.

In embodiments, two or more information items from the situation information may be applied together (e.g., mental activity and surrounding environment for the sitting posture may be applied at the same time), in which case predefined features may be used together (e.g., $f_{TPR}1+f_{TPR}2$) or a statistical value (e.g., $(f_{TPR}1+f_{TPR}2)/2$) may be used, and a feature may also be determined by, for example, applying a weight to mental activity rather than surrounding environment. The method of determining the CO features and TPR features is not limited thereto.

Figure 3:
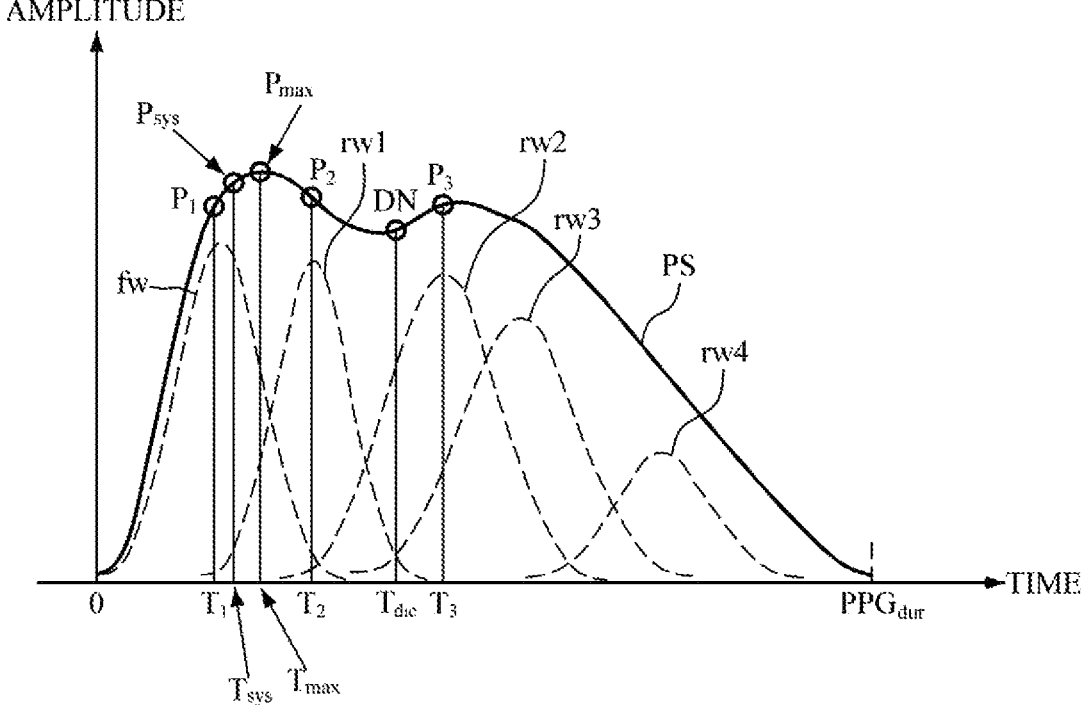
FIG. 3 is a diagram explaining a plurality of predefined cardiovascular features, according to an embodiment.

Examples of the plurality of predefined CO features (e.g., $f_{co}1$, $f_{co}2$, $f_{co}3$, $f_{co}4$, and $f_{co}5$) and/or TPR features (e.g., $f_{TPR}1$, $f_{TPR}2$, $f_{TPR}3$, $f_{TPR}4$, and $f_{TPR}5$) are shown in the following Table 3 and FIG. 3. However, the CO features and TPR features are not limited thereto.

TABLE 3

| No. | Examples of CO feature and/or TPR feature |
|---|---|
| 1 | Heart rate (HR) |
| 2 | $PPG_{area}$ |
| 3 | $P_3/P_{max}$ |
| 4 | $P_3/P_{sys}$ |
| 5 | $P_{max}/PPG_{area}$ |
| 6 | $1/PPG_{dur}$ |
| 7 | $1/(T_3 - T_1)$ |
| 8 | $1/(T_3 - T_{sys})$ |
| 9 | $1/(T_3 - T_{max})$ |
| 10 | $1/(T_2 - T_1)$ |
| 11 | $P_2/P_1$ |
| 12 | $P_3/P_{max}$ |

TABLE 3-continued

| No. | Examples of CO feature and/or TPR feature |
|---|---|
| 13 | $P_3/P_1$ |
| 14 | $P_3/P_2$ |

Herein, $PPG_{area}$ may denote an area of the PPG signal, and $PPG_{dur}$ may denote a time duration representing a period of the PPG signal. In this case, the area of the PPG signal may denote a total area of the PPG signal or an area corresponding to a predetermined proportion (e.g., 70%) of a total time duration $PPG_{dur}$.

$T_1$, $T_2$, $T_3$, $P_1$, $P_2$, and $P_3$ may denote times and amplitudes at maximum points of first to third component pulse waves, for example first component pulse wave fw, second component pulse wave rw1, and third component pulse wave rw2. In this case, $T_1$, $T_2$, and $T_3$ may respectively denote times at maximum points of the first to third component pulse waves fw, rw1, and rw2 in a second derivative signal of the PPG signal PS. In addition, $P_{max}$ may denote a maximum amplitude in one period (for example from 0 to $PPG_{dur}$) of the PPG signal PS or in a predetermined region of one period of the PPG signal PS, and $T_{max}$ may denote a time point of the maximum amplitude $P_{max}$. In this case, the predetermined region may refer to a systolic region, which may be a region from the beginning of the PPG signal to a time point $T_{dic}$ at which the dicrotic notch DN occurs, and $(T_{sys}, P_{sys})$ may denote an internal dividing point between two characteristic points $(T_1, P_1)$ and $(T_{max}, P_{max})$ when the characteristic points $(T_1, P_1)$ and $(T_{max}, P_{max})$ are extracted.

Next, the processor 120 may generate a blood pressure estimation model based on the determined cardiovascular features and the recognized situation information and posture information.

For example, the processor 120 may determine modeling coefficients of the blood pressure estimation model based on the recognized situation information and posture information.

Examples of modeling coefficients a and b for a predetermined feature $f_{TPR}1$ are shown in Table 4 and Table 5 below, and an example of $\Delta f_{TPR}$ generated based on $\Delta f_{TPR}1$ is represented by Equation 2 below. In this case, $\Delta f_{TPR}1$ corresponds to a variation in $f_{TPR}1$ compared to a calibration time, and $\Delta f_{TPR}$ corresponds to a variation in TPR feature compared to the calibration time.

TABLE 4

| $a(f_{TPR}1)$ | Sitting posture | Supine posture | Standing posture |
|---|---|---|---|
| Mental activity | 0.4 | 0.1 | 0.2 |
| Surrounding environment | 0.5 | 0.5 | 0.3 |
| Physical activity | 0.3 | 0.1 | 0.2 |

TABLE 5

| $b(f_{TPR}1)$ | Sitting posture | Supine posture | Standing posture |
|---|---|---|---|
| Mental activity | −0.01 | −0.01 | 0 |
| Surrounding environment | 0.1 | 0.2 | 0.15 |
| Physical activity | −0.2 | 0.1 | −0.1 |

$$\Delta f_{TPR} = a \times \Delta f_{TPR}1 + b \qquad \text{Equation 2}$$

For example, upon recognizing, by using the plurality of sensors, that a user has performed or is performing a mental activity and is in a sitting posture, the processor 120 may determine $f_{TPR}1$ as shown in Table 1, in which case the processor 120 may determine the modeling coefficients a and b to be 0.4 and −0.01, respectively, as shown in Table 4 and Table 5. In this case, the model in Equation 2 is an example, and various models, such as a linear model, a non-linear model, a machine learning model, etc., may also be used. Table 4 and Table 5 show examples of modeling coefficients for $f_{TPR}1$, and data associated with modeling coefficients for each of $f_{TPR}2$, $f_{TPR}3$, $f_{TPR}4$, and $f_{TPR}5$ may be prestored as shown in Table 4 and Table 5. In addition, in the same method of generating the estimation model for obtaining $\Delta f_{TPR}$ in Equation 2, the processor 120 may also generate an estimation model for obtaining $\Delta f_{co}$.

Next, the processor 120 may generate a blood pressure estimation model which may be represented by the Equation 3 and Equation 4 below. Further, the processor 120 may estimate a user's blood pressure according to the generated blood pressure estimation model.

$$BP_{est} = BP_{cal} + fun(\Delta f_{TPR}, \Delta f_{co}) \qquad \text{Equation 3}$$

$$BP_{est} = BP_{cal} + fun(a \times \Delta f_{TPR}k + b, a' \times \Delta f_{co}k' + b') \qquad \text{Equation 4}$$

Herein, $BP_{est}$ may denote an estimated blood pressure value, $BP_{cal}$ may denote a reference blood pressure, e.g., a blood pressure measured by a cuff at a calibration time, $\Delta f_{co}$ may denote a variation in CO feature compared to the calibration time, $\Delta f_{TPR}k$ and $\Delta f_{co}k'$ may denote variations in cardiovascular features determined based on the situation information and posture information which are recognized using sensor data, and a, b, a', and b' may denote modeling coefficients selected based on the determined cardiovascular features and the situation information and the posture information.

For example, the processor 120 may extract a feature (e.g., $P_2/P_1$ as an example of $f_{TPR}1$) corresponding to cardiovascular features (e.g., CO feature and TPR feature) determined based on the PPG signal acquired by the PPG sensor, may apply the extracted features to the blood pressure estimation model along with the determined modeling coefficients, and may estimate blood pressure by linearly combining a result of the application and the reference blood pressure.

In this case, the processor 120 may receive user characteristics (e.g., height, age, weight, gender, vascular compliance, etc.) input by a user through an interface, and may estimate blood pressure by correcting the blood pressure estimation model generated based on the user characteristics input by the user.

When blood pressure is estimated by an electronic device attached to a local body part, a value may be inconsistent depending on a user's activity or environment. Therefore, in embodiments, blood pressure may be estimated by reflecting or considering activity or environment factors of a user prior to estimation by using a plurality of sensors, thereby increasing the accuracy of blood pressure estimation.

Figure 4:
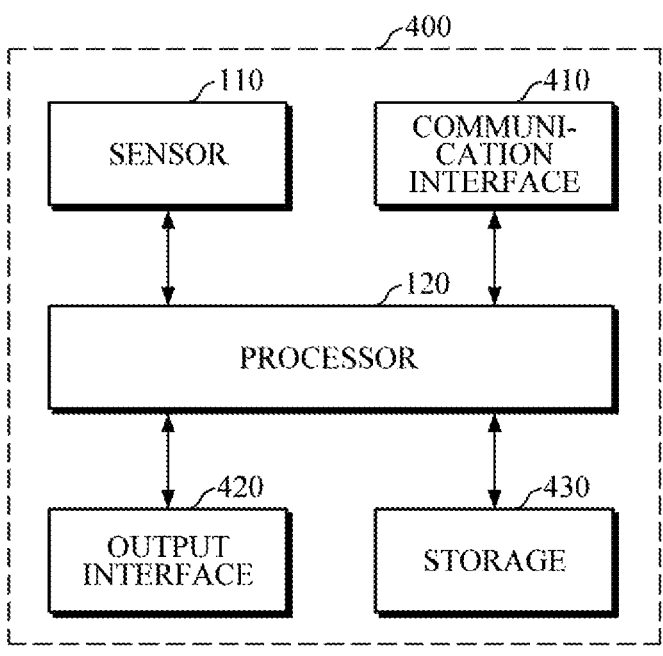
FIG. 4 is a block diagram illustrating an apparatus for estimating blood pressure, according to an embodiment.

FIG. 4 is a block diagram illustrating an apparatus for estimating blood pressure according to an embodiment of the present disclosure.

Referring to FIG. 4, an apparatus 400 for estimating blood pressure may include the sensor 110, the processor 120, a communication interface 410, an output interface 420, and a storage 430. Examples of the sensor 110 and the processor 120 are described in detail above, and therefore a redundant or duplicative description thereof may be omitted below.

The communication interface 410 may be electrically connected to the processor 120 and may transmit and receive data with an external electronic device using various communication technologies under the control of the processor 120. The data may include, for example, a reference blood pressure, an equation for estimating blood pressure, a blood pressure estimation result, and the like. Examples of the external electronic device may include a blood pressure measuring device such as a cuff sphygmomanometer, a smartphone, a tablet PC, a desktop computer, a laptop computer, a wearable device, and the like. However, the electronic device is not limited thereto. In this case, the communication technologies may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, 3G, 4G, 5G, and 6G communications, and the like.

The output interface 420 may output processing results of the sensor 110 and/or the processor 120, and may provide the results to a user. The output interface 420 may provide the user with blood pressure information by various visual/non-visual methods using a visual output module such as a display, an audio output module such as a speaker and the like, or a haptic module by vibrations, tactile sensation, and the like.

In addition, the output interface 420 may include a display. For example, the output interface 420 may display a blood pressure value, estimated by the processor 120, on the display. In this case, if the estimated blood pressure value falls outside of a normal range, the output interface 420 may provide a user with information, such as a warning, by changing color, line thickness, etc., or by displaying the abnormal value along with the normal range, so that the user may easily recognize the information.

Further, with or without the visual displaying by the display, the output interface 420 may provide the user with the estimated blood pressure value in a non-visual manner by voice, vibrations, tactile sensation, and the like using an audio output module such as a speaker and the like, or a haptic module.

The display may include touch circuitry adapted to detect a touch, and/or sensor circuitry (e.g., pressure sensor, etc.) adapted to measure the intensity of force incurred by the touch. An audio module may convert a sound into an electrical signal or vice versa. The audio module may obtain the sound using the input device, or may output the sound using the sound output device, and/or a speaker and/or a headphone of another electronic device directly or wirelessly connected to the electronic device. A haptic module may convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

Figure 5:
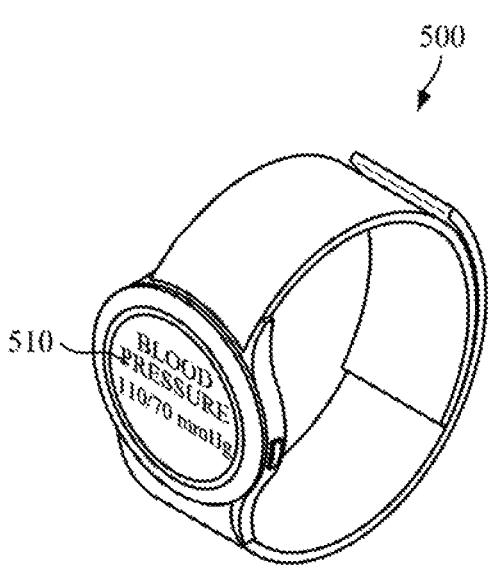
FIG. 5 is a diagram illustrating an example of displaying information about estimated blood pressure on a display of an apparatus for estimating blood pressure according to an embodiment.

FIG. 5 is a diagram illustrating an example of displaying information about estimated blood pressure on a display of an apparatus for estimating blood pressure according to an embodiment of the present disclosure.

Referring to FIG. 5, a display 510, which may be disposed on a front surface of a wearable device 500, may display an estimated blood pressure value. In addition, the output interface 420 may provide information about high blood pressure or low blood pressure to a user based on the estimated blood pressure, and may also provide the user with health guidance information based on the provided information. The output of the blood pressure value and information thereon to the display 510 is not limited thereto and may vary.

Referring back to FIG. 4, the storage 430 may store data used by the sensor 110 and/or the processor 120, and/or processing results of the sensor 110 and/or the processor 120. For example, the storage 430 may store a blood pressure estimation model, a reference blood pressure, user characteristics (e.g., height, age, weight, gender, vascular compliance, etc.), an estimated blood pressure value, data acquired by a plurality of sensors, CO features and TPR features, modeling coefficients, and the like.

The storage 430 may include a storage medium having at least one type of a flash memory type, a hard disk type, a multimedia card micro type, a card type (e.g., a Secure Digital (SD) memory card, an XD memory card, etc.), a random access memory (RAM), a static random access memory (SRAM), a read-only memory (ROM), an electrically erasable programmable read-only memory (EEPROM), a programmable read-only memory (PROM), a magnetic memory, a magnetic disc, or an optical disc, etc., but is not limited thereto.

Figure 6:
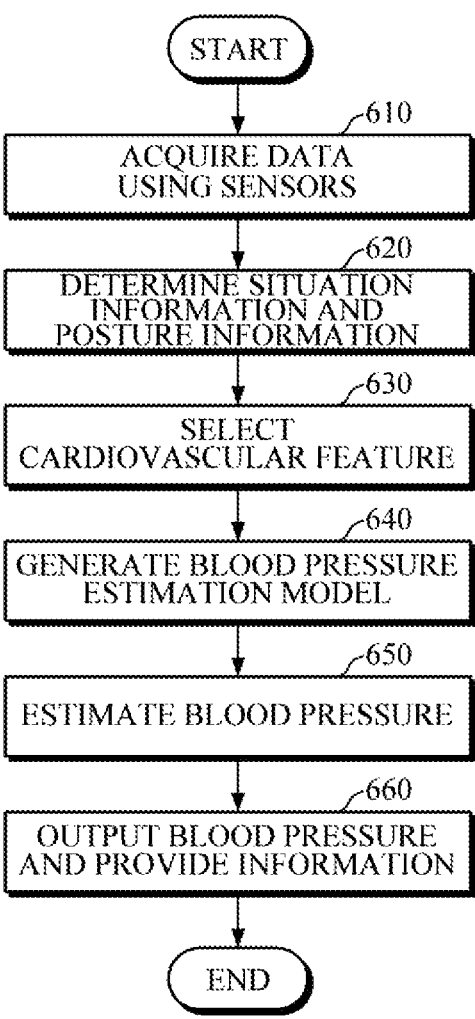
FIG. 6 is a flowchart illustrating a method of estimating blood pressure according to an embodiment.

FIG. 6 is a flowchart illustrating a method of estimating blood pressure according to an embodiment of the present disclosure. The method of FIG. 6 may be performed by any of the elements discussed above, for the apparatus 100, the apparatus 400, or any of the elements included therein.

First, the apparatus for estimating blood pressure may acquire data using a plurality of sensors at operation 610. In this case, the plurality of sensors may include at least one of an acceleration sensor, an angular velocity sensor, a geomagnetic sensor, a gyro sensor, a temperature sensor, a pressure sensor, and a photoplethysmogram (PPG) sensor.

Then, the apparatus for estimating blood pressure may recognize, identify, or determine situation information and posture information prior to estimation of a user's blood pressure based on the data acquired by the plurality of sensors at operation 620. In this case, the situation information may include at least one of the user's mental activity, physical activity, and surrounding environment, and the posture information may include or indicate at least one of a sitting posture, supine posture, and standing posture.

Subsequently, the apparatus for estimating blood pressure may select one of a plurality of predefined cardiovascular features based on the determined situation information and posture information at operation 630. In this case, the cardiovascular features may include CO features and total peripheral TPR features that may be obtained from the PPG signal, and the apparatus for estimating blood pressure may determine at least one or more of the plurality of predefined CO features and TPR features.

Next, the apparatus for estimating blood pressure may generate a blood pressure estimation model based on the determined cardiovascular feature and the recognized situation information and posture information at operation 640. In this case, the apparatus for estimating blood pressure may determine modeling coefficients of the blood pressure estimation model based on the recognized situation information and posture information.

Then, the apparatus for estimating blood pressure may estimate blood pressure of the user based on the generated blood pressure estimation model at operation 650. For example, the apparatus for estimating blood pressure may extract a feature value, corresponding to the determined cardiovascular feature, based on the PPG signal, may apply the extracted feature value to the generated blood pressure estimation model, and may estimate the blood pressure by linearly combining a result of the application and a reference blood pressure. In this case, the reference blood pressure may be blood pressure measured by a cuff at a calibration time.

Subsequently, the apparatus for estimating blood pressure may output the estimated blood pressure of the user by a visual or non-visual method or may provide the user with information about the blood pressure at operation 660.

FIGS. 7A to 10 are diagrams illustrating examples of various structures of an electronic device including an apparatus for estimating blood pressure.

The electronic device may include, for example, various types of wearable devices, e.g., a smart watch, a smart band, smart glasses, smart earphones, a smart ring, a smart patch, and a smart necklace, and a mobile device such as a smartphone, a tablet PC, etc., or home appliances or various Internet of Things (IoT) devices (e.g., home IoT device, etc.) based on Internet of Things (IoT) technology.

The electronic device may include a sensor device, a processor, an input device, a communication module, a camera module, an output device, a storage device, and a power module. All of the components of the electronic device may be integrally mounted in a specific device, or the components may be distributed in two or more devices. The sensor device may further include the sensor 110 of the apparatus 100 for estimating blood pressure which may include, for example, a PPG sensor, a gyro sensor, a Global Positioning System (GPS), an acceleration sensor, an angular velocity sensor, a geomagnetic sensor, a temperature sensor, a pressure sensor, and the like.

The processor may execute programs, stored in the storage device, to control components connected to the processor, and may perform various data processing or computation, including estimation of blood pressure. The processor may include a main processor, e.g., a central processing unit (CPU) or an application processor (AP), etc., and an auxiliary processor, e.g., a graphics processing unit (GPU), an image signal processor (ISP), a sensor hub processor, or a communication processor (CP), etc., which is operable independently from, or in conjunction with, the main processor.

The input device may receive a command and/or data to be used by each component of the electronic device, from a user and the like. The input device may include, for example, a microphone, a mouse, a keyboard, or a digital pen (e.g., a stylus pen, etc.).

The communication module may support establishment of a direct (e.g., wired) communication channel and/or a wireless communication channel between the electronic device and other electronic device, a server, or the sensor device within a network environment, and performing of communication using the established communication channel. The communication module may include one or more communication processors that are operable independently from the processor and supports a direct communication and/or a wireless communication. The communication module may include a wireless communication module, e.g., a cellular communication module, a short-range wireless communication module, or a global navigation satellite system (GNSS) communication module, etc., and/or a wired communication module, e.g., a local area network (LAN) communication module, a power line communication (PLC) module, and the like. These various types of communication modules may be integrated into a single chip, or may be separately implemented as multiple chips. The wireless communication module may identify and authenticate the electronic device in a communication network using subscriber information (e.g., international mobile subscriber identity (IMSI), etc.) stored in a subscriber identification module.

The camera module may capture still images or moving images. The camera module may include a lens assembly having one or more lenses, image sensors, image signal processors, and/or flashes. The lens assembly included in the camera module may collect light emanating from a subject to be imaged.

The output device may visually/non-visually output data generated or processed by the electronic device. The output device may include a sound output device, a display device, an audio module, and/or a haptic module.

The sound output device may output sound signals to the outside of the electronic device. The sound output device may include a speaker and/or a receiver. The speaker may be used for general purposes, such as playing multimedia or playing record, and the receiver may be used for incoming calls. The receiver may be implemented separately from, or as part of, the speaker.

The display device may visually provide information to the outside of the electronic device. The display device may include, for example, a display, a hologram device, or a projector and control circuitry to control the devices. The display device may include touch circuitry adapted to detect a touch, and/or sensor circuitry (e.g., pressure sensor, etc.) adapted to measure the intensity of force incurred by the touch.

The audio module may convert a sound into an electrical signal or vice versa. The audio module may obtain the sound using the input device, or may output the sound using the sound output device, and/or a speaker and/or a headphone of another electronic device directly or wirelessly connected to the electronic device.

The haptic module may convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

The storage device may store operating conditions used operating the sensor device, and various data required for other components of the electronic device. The various data may include, for example, input data and/or output data for software and instructions related thereto. The storage device may include a volatile memory and/or a non-volatile memory.

The power module may manage power supplied to the electronic device. The power module may be implemented as part of, for example, a power management integrated circuit (PMIC). The power module may include a battery, which may include a primary cell which is not rechargeable, a secondary cell which is rechargeable, and/or a fuel cell.

Figure 7A:
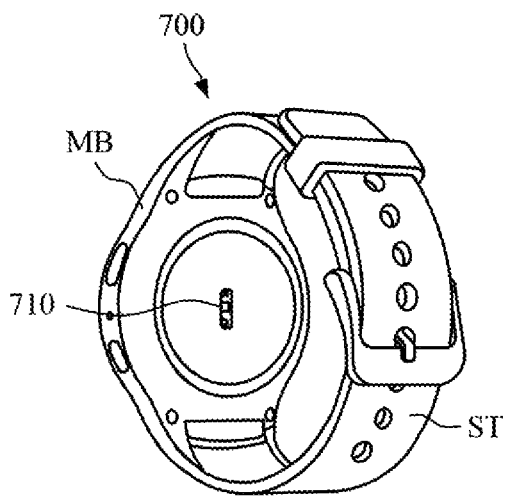
FIGS. 7A to 10 are diagrams illustrating examples of various structures of an electronic device including an apparatus for estimating blood pressure, according to embodiments.

Referring to FIG. 7A, the electronic device may be implemented as a smart watch-type wearable device 700 which includes a main body MB and a wrist strap ST.

The main body MB may be formed in various shapes. A battery may be embedded in the main body MB and/or the strap ST to supply power to various components of the wearable device. The strap ST may be connected to two ends of the main body to allow the main body to be worn on a user's wrist, and may be flexible in order to be wrapped around the user's wrist. The strap ST may include a first strap and a second strap which are separated from each other. One end of each of the first strap and the second strap may be connected to a side of the main body MB, and the other end may include a fastener or connector which may be used to connect the first strap and the second strap to each other. In this case, the fastener or connector may be include other. One or more of a magnetic fastening, a Velcro fastening, a pin fastening, and the like, but is not limited thereto. Further, the strap ST is not limited thereto, and may be integrally formed as a non-detachable band, or may be a single strap configured to connect to itself.

The main body MB may include a sensor 710, a processor, an output interface, a storage, and a communication interface. However, depending on the size and shape of a form factor and the like, one or more of the output interface, the storage, and the communication interface may be omitted.

The sensor 710 may include a plurality of sensors for acquiring data from a user when an object comes into direct or indirect contact with the main body, and example of the sensors may include an acceleration sensor, an angular velocity sensor, a geomagnetic sensor, a gyro sensor, a temperature sensor, a pressure sensor, and a photoplethysmogram (PPG) sensor. In this case, the sensor 710 may be disposed on a rear surface of the main body MB to be placed in contact with the upper part of a user's wrist when the main body MB is worn on the user's wrist, in order to acquire data for estimating blood pressure.

The processor mounted in the main body MB may be electrically connected to various components as well as the sensor 710. For example, while the strap is wrapped around the wrist and the main body is worn on the wrist, the processor may recognize situation information and posture information prior to estimation of a user's blood pressure based on data acquired by the plurality of sensors, may determine one of a plurality of predefined cardiovascular features based on the recognized situation information and posture information, to generate a blood pressure estimation model based on the determined cardiovascular feature and the recognized situation information and posture information, and may estimate blood pressure based on the generated blood pressure estimation model. In this case, the situation information may include at least one of the user's mental activity, physical activity, and surrounding environment, and the posture information may include or indicate at least one of the user's sitting posture, supine posture, and standing posture.

A display DP may be provided on a front surface of the main body MB, and various application screens, including an estimated blood pressure value, time information, received message information, etc., may be displayed on the display DP.

Figure 7B:
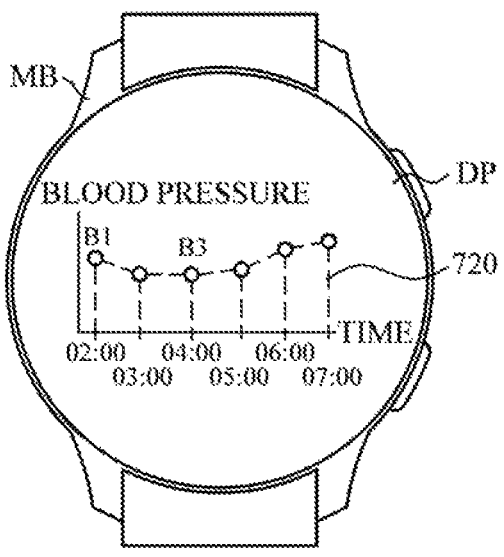

For example, the output interface may display a blood pressure estimation result on the display DP of the main body MB. Referring to FIG. 7B, for example, if blood pressure is automatically measured on an hourly basis during sleep at night, the output interface may display a measurement result in a visual graph 720. In this case, if the user selects a graphic object B1 in the graph 720, the output interface may display an estimated blood pressure value at a corresponding time (e.g., 2:00 a.m.) on a separate display screen, and if the user selects a graphic object B3, the output interface may display an estimated blood pressure value at a corresponding time (e.g., 4:00 a.m.) on a separate display screen. However, these examples are merely for convenience of explanation, and the output interface is not limited thereto.

13

14

Figure 8:
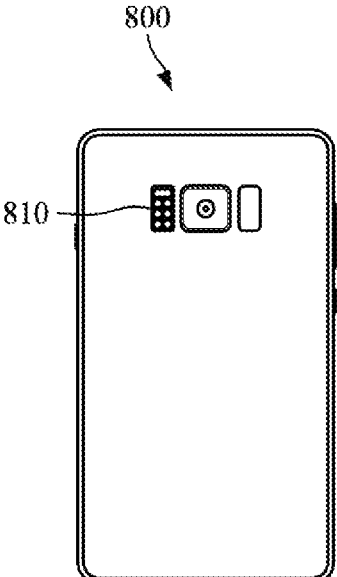

Referring to FIG. 8, the electronic device may be implemented as a mobile device 800 such as a smartphone.

The mobile device 800 may include a housing and a display panel. The housing may form an exterior of the mobile device 800. The housing may have a first surface, on which a display panel and a cover glass may be disposed sequentially, and the display panel may be exposed to the outside through the cover glass. A sensor 810, a camera module and/or an infrared sensor, and the like may be disposed on a second surface of the housing.

For example, a plurality of sensors for acquiring data from a user may be disposed on a rear surface of the mobile device 800, and a fingerprint sensor disposed on the front surface of the mobile device 800, a power button or a volume button disposed on a side surface thereof, sensors disposed on other positions of the front and rear surfaces of the mobile device 800, and the like may be provided to estimate the user's blood pressure.

For example, when a user transmits a request for estimating blood pressure by executing an application and the like installed in the mobile device 800, the mobile device 800 may acquire data using the sensor 810, and may estimate blood pressure using the processor in the mobile device 800.

Figure 9:
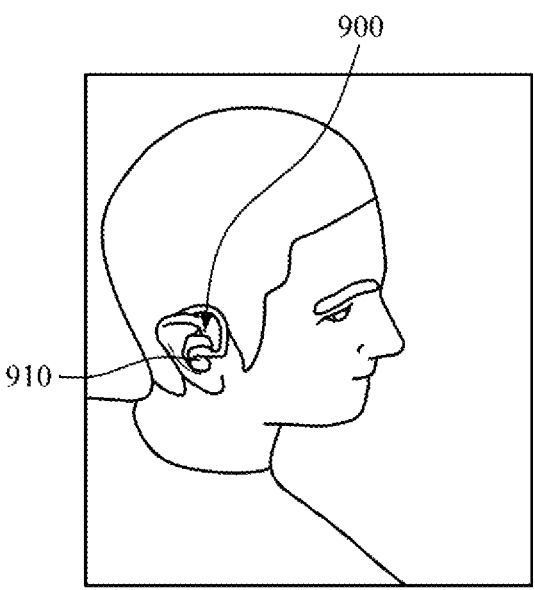

Referring to FIG. 9, the electronic device may be implemented as an ear-wearable device 900.

The ear-wearable device 900 may include a main body and an ear strap. A user may wear the ear-wearable device 900 by hanging the ear strap on an auricle. The ear strap may be omitted depending on a shape of the ear-wearable device 900. The main body may be inserted into the external auditory meatus. A sensor 910 may be mounted in the main body. The ear-wearable device 900 may provide a user with a blood pressure estimation result as sound, or may transmit the estimation result to an external device, e.g., a mobile device, a tablet PC, a personal computer, etc., through a communication module provided in the main body.

Figure 10:
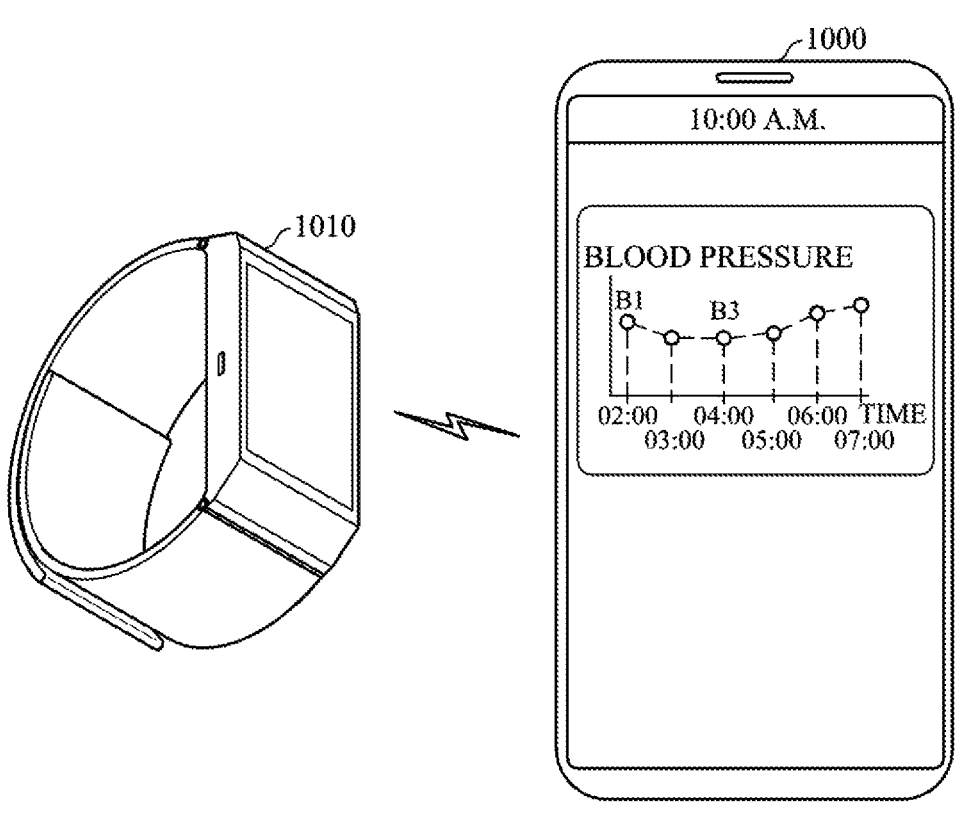

Referring to FIG. 10, the electronic device may be implemented as a combination of a wristwatch-type wearable device and a mobile device such as a smartphone. For example, a memory, a communication interface, and a processor for estimating blood pressure may be mounted in a main body of the mobile device 1000. Upon receiving a request for estimating blood pressure, the processor of the mobile device 1000 may control the communication interface to communicate with a communication module, mounted in a main body of a wearable device 1010, to obtain data for estimating blood pressure. Further, upon receiving data from the wearable device 1010, the processor may estimate blood pressure based on the received data.

Embodiments may be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the present invention can be readily deduced by programmers of ordinary skill in the art to which the invention pertains.

The present disclosure has been described herein with regard to various embodiments. However, it will be obvious to those skilled in the art that various changes and modifications can be made without changing technical conception and essential features of the present disclosure. Thus, it is clear that the above-described embodiments are illustrative in all aspects and are not intended to limit the present disclosure.

What is claimed is:

1. An apparatus for estimating blood pressure, the apparatus comprising:
   a plurality of sensors comprising a photoplethysmogram (PPG) sensor; and
   at least one processor configured to:
   determine situation information and posture information of a user based on data acquired by the plurality of sensors,
   select a cardiac output (CO) feature and a total peripheral resistance (TPR) feature from among a plurality of predetermined CO features and TPR features based on the situation information and the posture information,
   generate a blood pressure estimation model based on the CO feature and the TPR feature, the situation information, and the posture information, and
   estimate a blood pressure of the user based on the generated blood pressure estimation model,
   wherein the situation information comprises information about at least one of a mental activity, a physical activity, and a surrounding environment of the user, and
   wherein the posture information indicates at least one of a sitting posture, a supine posture, and a standing posture,
   wherein the at least one processor is further configured to determine a modeling coefficient of the blood pressure estimation model based on the situation information and the posture information.

2. The apparatus of claim 1, wherein the plurality of sensors comprises at least one of an acceleration sensor, an angular velocity sensor, a geomagnetic sensor, a gyroscopic sensor, a temperature sensor, and a pressure sensor.

3. The apparatus of claim 2, wherein the at least one processor is further configured to:
   extract a feature value corresponding to the CO feature and the TPR feature,
   apply the extracted feature value to the generated blood pressure estimation model, and
   estimate the blood pressure of the user by linearly combining a reference blood pressure with a result obtained from the generated blood pressure estimation model.

4. The apparatus of claim 3, wherein the reference blood pressure is measured by a cuff at a calibration time.

5. The apparatus of claim 2, wherein the PPG sensor comprises a light source configured to emit light to an object, and a detector configured to detect the light after the light is reflected by or scattered from the object.

6. The apparatus of claim 1, further comprising an output interface configured to provide the estimated blood pressure to the user visually or non-visually.

7. A method of estimating blood pressure, the method comprising:
   acquiring data from among a plurality of sensors, the plurality of sensors comprising a photoplethysmogram (PPG) sensor;
   determining situation information and posture information of a user based on the acquired data by the plurality of sensors;
   selecting a cardiac output (CO) feature and a total peripheral resistance (TPR) feature from among a plurality of predetermined CO features and TPR features based on the situation information and the posture information;

generating a blood pressure estimation model based on the CO feature, the TPR feature, the cardiovascular feature, the situation information, and the posture information; and estimating a blood pressure of the user based on the generated blood pressure estimation model, wherein the situation information comprises information about at least one of a mental activity, a physical activity, and a surrounding environment of the user, and wherein the posture information indicates at least one of a sitting posture, a supine posture, and a standing posture, wherein the generating of the blood pressure estimation model comprises determining a modeling coefficient of the blood pressure estimation model based on the situation information and the posture information.

8. The method of claim 7, wherein the estimating of the blood pressure comprises:

extracting a feature value corresponding to the selected cardiac output (CO) feature and total peripheral resistance (TPR) feature;

applying the extracted feature value to the generated blood pressure estimation model, and estimating the blood pressure of the user by linearly combining a reference blood pressure with a result obtained from the generated blood pressure estimation model.

9. The method of claim 8, wherein the reference blood pressure is measured by a cuff at a calibration time.

10. The method of claim 7, further comprising outputting the estimated blood pressure to the user visually or non-visually.

* * * * *